United States Patent [19]

Goldstein et al.

[11] Patent Number: 5,045,701

[45] Date of Patent: Sep. 3, 1991

[54] INFRARED SPECTROPOLARIMETER

[75] Inventors: Dennis H. Goldstein, Niceville, Fla.; Russell A. Chipman, Madison, Ala.

[73] Assignee: The United States of America as represented by the Secretary of the Air Force, Washington, D.C.

[21] Appl. No.: 413,414

[22] Filed: Sep. 27, 1989

[51] Int. Cl.$^5$ .............................................. G01J 3/447
[52] U.S. Cl. ..................................... 250/339; 250/353
[58] Field of Search ............... 250/339, 340, 341, 353, 250/225; 356/367, 368, 366

[56] References Cited

U.S. PATENT DOCUMENTS

| | | |
|---|---|---|
| 3,155,762 | 11/1964 | Gillham et al. |
| 3,361,028 | 1/1968 | Kuttner |
| 3,545,865 | 12/1970 | Hooper |
| 3,636,359 | 1/1972 | Hooper ............................... 250/225 |
| 3,741,660 | 6/1973 | Abu-Shumays et al. ............ 250/225 |
| 4,440,013 | 4/1984 | Adams ................................. 73/23.1 |
| 4,594,509 | 6/1986 | Simon et al. ........................ 250/338 |
| 4,917,461 | 4/1990 | Goldstein ............................ 350/394 |

OTHER PUBLICATIONS

"Photo Polarimetric Measurement of the Mueller Matrix by Fourier Analysis of a Single Detected Signal", R. M. A. Azzam, Opt. Lett. 2(6): 148 (1978).
"Mueller Matrix Ellipsometry with Imperfect Compensators", P. S. Hauge, J. Opt. Soc. Am. 68(11): 1519 (1978).

Primary Examiner—Jack I. Berman
Assistant Examiner—Richard Hanig
Attorney, Agent, or Firm—Bobby D. Scearce; Donald J. Singer

[57] ABSTRACT

An infrared spectropolarimeter system for making spectroscopic measurements of electro-optic properties of materials over a large wavelength range in the infrared is described which comprises in combination a spectrometer having a sample region for receiving a sample for making spectroscopic measurements thereon and a source of light for providing a sample beam of selected wavelength for projection through the sample region, the sample region defined between a first focusing element for selectively focusing the sample beam within the sample region and a second focusing element for collimating the sample beam and providing an output beam for analysis, first and second polarizers between the focusing elements with the sample region therebetween for selectively polarizing the sample beam, first and second rotatable optical retarders between the polarizers with the sample region therebetween for selectively retarding one linear polarization component with respect to the orthogonal component of the sample beam, and a detector for analyzing the output beam.

4 Claims, 4 Drawing Sheets

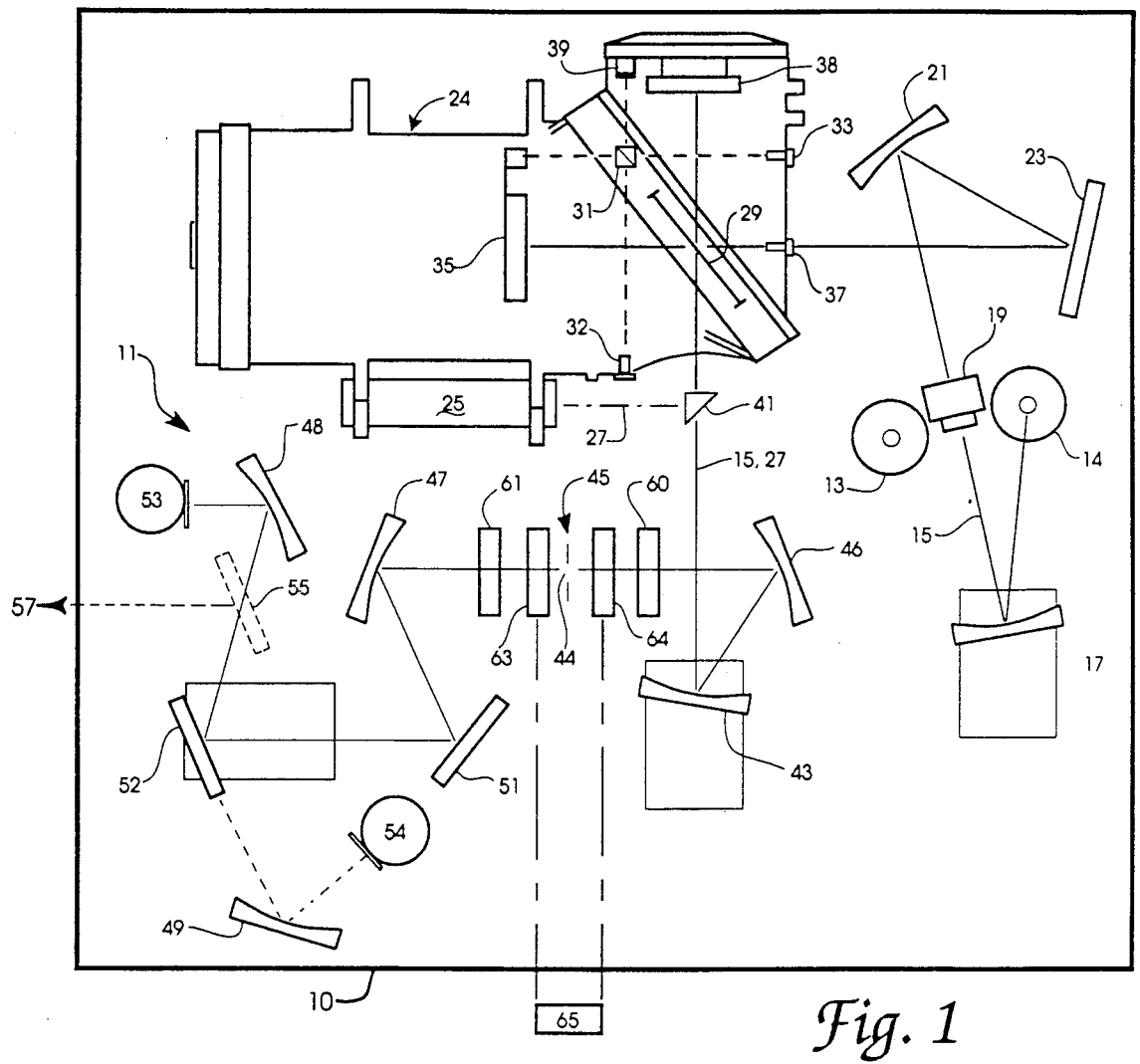
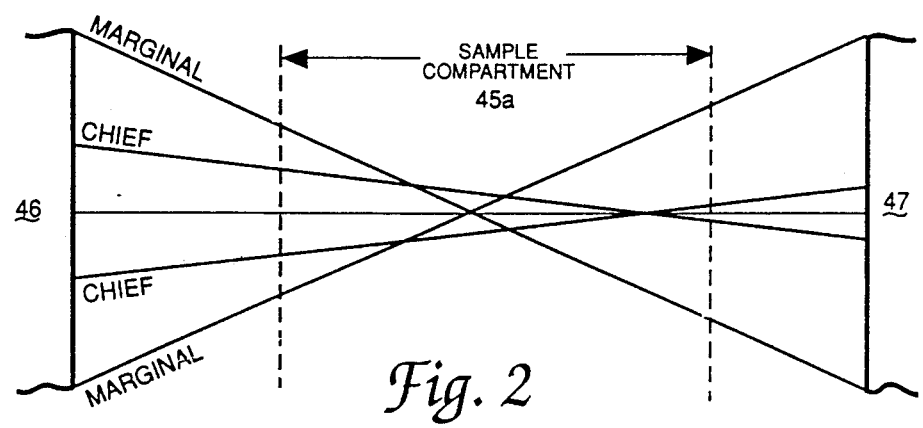

INFRARED SPECTROPOLARIMETER

RIGHTS OF THE GOVERNMENT

The invention described herein may be manufactured and used by or for the Government of the United States for all governmental purposes without the payment of any royalty.

CROSS-REFERENCE TO RELATED APPLICATION

The invention described herein is related to copending application Ser. No. 07/298,072 filed Jan. 11, 1989 entitled "Achromatic Infrared Retarder" now U.S. Pat. No. 4,917,461 dated Apr. 17, 199 .

BACKGROUND OF THE INVENTION

The present invention relates generally to infrared spectropolarimeters, and more particularly to a spectropolarimeter system including Fourier transform infrared spectroscopy and polarimetry.

A polarimeter is an optical instrument for measuring the polarization state of a light beam and polarizing and retarding properties of materials. A spectropolarimeter is an instrument which incorporates a monochromator as a radiation source and makes repetitive spectroscopic measurements as polarization state is changed incrementally. An infrared spectropolarimeter is used to make spectroscopic measurements of the polarization properties of materials in the infrared. However, neither polarimeters nor currently available spectropolarimeters can make spectroscopic measurements of polarization properties easily, with high resolution and with good energy efficiency.

The invention comprises an infrared spectropolarimeter for making spectroscopic measurements of polarization properties and other electro-optic properties of materials over large wavelength intervals in the infrared, and combines Fourier transform infrared spectroscopy and polarimetry. The sample region of the invention includes an achromatic polarizer and retarder on either side of a sample and individually mounted in computer controlled rotating stages for orientation control. Data is taken as a function of wavelength and polarizing element orientation. The result is a 4×4 Mueller matrix describing the polarizing, retarding, and scattering properties of the sample as functions of wavelength and, if so configured, electric and magnetic field strength.

It is therefore a principal object of the invention to provide a novel infrared spectropolarimeter system.

It is a further object to provide a spectropolarimeter system combining Fourier transform infrared spectroscopy and polarimetry.

These and other objects of the invention will become apparent as the detailed description of representative embodiments proceeds.

SUMMARY OF THE INVENTION

In accordance with the foregoing principles and objects of the invention, an infrared spectropolarimeter system for making spectroscopic measurements of electro-optic properties of materials over a large wavelength range in the infrared is described which comprises in combination a spectrometer having a sample region for receiving a sample for making spectroscopic measurements thereon and a source of light for providing a sample beam of selected wavelength for projection through the sample region, the sample region defined between a first focusing element for selectively focusing the sample beam within the sample region and a second focusing element for collimating the sample beam and providing an output beam for analysis, first and second polarizers between the focusing elements with the sample region therebetween for selectively polarizing the sample beam, first and second rotatable optical retarders between the polarizers with the sample region therebetween for selectively retarding one linear polarization component with respect to the orthogonal component of the sample beam, and a detector for analyzing the output beam.

DESCRIPTION OF THE DRAWINGS

The invention will be more clearly understood from the following detailed description of representative embodiments thereof read in conjunction with the accompanying drawings wherein:

FIG. 1 is a schematic plan view of an infrared spectropolarimeter system of the invention;

FIG. 2 is a schematic illustration of the marginal and chief rays through the sample compartment of the FIG. 1 system;

DETAILED DESCRIPTION

Figure 3:
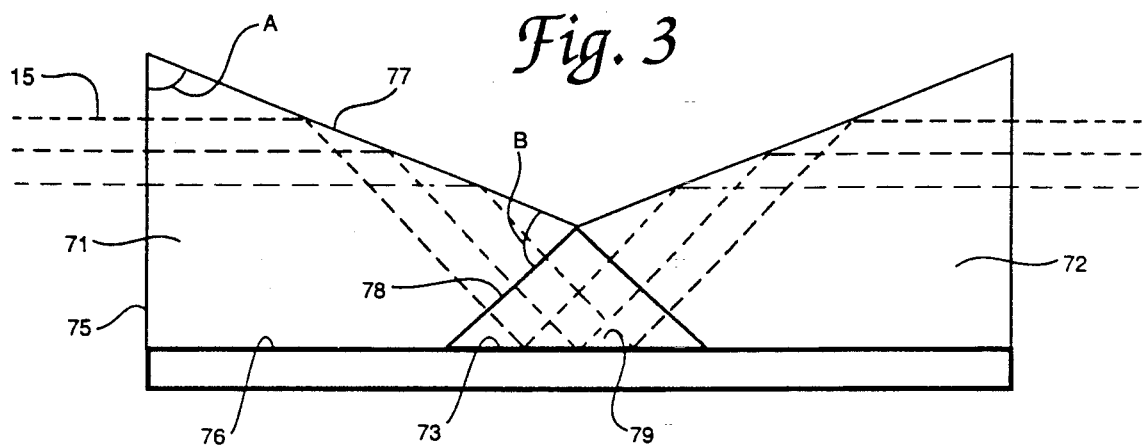
FIG. 3 shows the path of a sample beam through the achromatic infrared retarder in the sample region of the FIG. 1 system.

Referring now to the drawings. FIG. 1 shows a schematic plan view of an infrared spectropolarimeter system 10 according to the invention. System 10 includes a modified Fourier transform infrared spectrometer portion 11 and is otherwise configured to take repeated spectra of various orientations of polarization elements inside the sample compartment. FIG. 1 shows schematically a modified Nicolet 6000 Fourier transform (FT) infrared (IR) spectrometer, although substantially any FT spectrometer could be used as would occur to the skilled artisan in assembling system 10 according to the teachings hereof. Spectrometer portion 11 typically includes one or more sources 13,14 for generating a beam 15 of selected wavelength(s). Controllably positionable spherical mirror 17 focuses beam 15 onto and through aperture 19 for collimation by spherical mirror 21 and direction by flat mirror 23 to Michelson interferometer section 24. A preselected small entrance aperture 19 size (typically 6.35 mm but variable) limits the field of view of the interferometer. Beam 15 remains collimated until reaching sample region 45 described below. Section 24 includes IR beamsplitter 29, white light beamsplitter 31, white light source 32, white light detector 33, movable interferometer mirror 35, laser detector 37, and fixed flat mirrors 38,39; He-Ne reference laser 25 generates laser beam 27 directed through beamsplitter 41. Beams 15,27 are directed by a controllable flat mirror 43 into contact with sample 44 within sample region 45 defined between off-axis parabolic mirrors 46,47. Mirrors 46,47 are each typically about 9.3 inches in focal length; mirror 46 focuses beam 15 at a point about midway of sample region 45. Sample 44 is located somewhat asymmetrically with respect to mirrors 46,47. Spherical mirrors 48,49 cooperating with flat mirror 51 and controllable flat mirror 52 direct the resulting beam to detectors 53,54; beamsplitter 55 may direct a portion of the sample beam to remote detector 57.

In accordance with the principal teachings of the invention. polarizers 60,61 and retarders 63,64 are disposed on either side of sample 44 within sample region 45 as suggested in FIG. 1. Retarders 63,64 are disposed immediately adjacent sample 44 and include motorized mounts rotatable under computer 65 control.

Referring additionally to FIG. 2, shown therein is a diagram of the marginal and chief rays of beam 15 through sample region 45. The location of sample compartment 45a is indicated so that the clear aperture may be ascertained. The marginal ray remains fixed when interferometer 35 mirror moves, but the chief ray moves. At the source end of sample compartment 45a. the clear aperture is about 35 mm, and at the detector end about 33 mm. At the marginal ray focus, the clear aperture required is about 7 mm.

The function of polarizers 60,61 within sample region 45 is to selectively polarize beam 15 transmitted through sample region 45. Commercially available polarizers which may be used may include wire grid polarizers and crystal prism polarizers such as Glan-Thompson prisms. A wire grid polarizer is preferable for use in the 3-14 micron spectral range because of the compactness, high transmission, large clear aperture availability, lack of beam offset or angular displacement at normal incidence, and absence of polarization dependence of the ray angle through the polarizer by which it is characterized. A wire grid polarizer comprises an infrared transparent substrate on which are deposited parallel lines of conducting material. The polarization parallel to the lines is absorbed, while polarization perpendicular to the lines is transmitted with little attenuation. For the 3-14 micron range, the grid spacing is typically about 0.25 to 0.5 micron. Clear apertures of 1.5 inches are available. Typical wire grid polarizers are available commercially from Molectron Detector, Inc. (manufactured by Cambridge physical Sciences, England).

In system 10, two rotating quarter wave linear retarders 63,64 are required within sample region 45 as suggested in FIG. 1. An optical retarder is an optical element designed to retard one linear polarization component with respect to the orthogonal component to produce a selected phase shift between the two components. Rotation of retarders 63,64 is required in order to modulate the different Mueller matrix elements onto intensity variations at separate angular frequencies as discussed below. If retarders 63,64 are not quarter wave, the modulation is reduced. At wavelengths where retardance is 0 or $2n\pi$, the detected intensity is not modulated as the retarders rotate, and the polarimetric information is lost. Thus it is highly desirable that retarders 63,64 be nearly achromatic, that is, having retardance which is nearly constant across the wavelength range of interest; quarter wave retarders generally operate with monochromatic or narrow band light. In the operation of system 10, however. retarders 63,64 are calibrated and the observed retardances are used to compensate the recorded data for the loss of modulation associated with any observed chromatic variation of retardance. With monochromatic retarders, modulation is reduced, accuracy is reduced, but the basic function of the system is unaltered.

Two retarder types in common use are a total internal reflection prism and a waveplate. In a total internal reflection prism a specific phase shift occurs between the s and p components of light (linear retardance) on total internal reflection, depending on refractive index (usually wavelength dependent) of the material comprising the prism. The retardance of the prism is independent of thickness and variation of retardance with wavelength is substantially less than that of the waveplate. A common retarder of the prism type is known as a Fresnel rhomb which has desirably low wavelength dependence but has undesirably large beam offset associated with its use and is undesirably large; for example, a Fresnel rhomb for the infrared made of zinc selenide (ZnSe) having a clear aperture of 0.95 inch has a beam offset of 1.66 inches and a length of 3.65 inches. Infrared Fresnel rhombs are available commercially.

The waveplate quarter wave retarder consists of a plane parallel plate of birefringent material with the crystal axis oriented perpendicular to the intended propagation direction of an incident light beam; plate thickness is selected such that plate thickness times the birefringence (difference between ordinary and extraordinary refractive indices of the plate material) equals an integral number of quarter wavelengths of the incident beam. For an odd integer number, a quarter wave retarder obtains; for the integer equal to one, the plate is very thin and is referred to as a zero order waveplate. Retardance of the zero order waveplate necessarily varies with wavelength unless by coincidence the birefringence is linearly proportional to wavelength. Since this does not occur in practice, the waveplate has only approximate quarter wave retardance over a small wavelength range. For higher order waveplates (odd integer >1) the effective wavelength range for quarter wave retardance is even smaller. The achromatic range of a waveplate retarder can be enlarged with combinations of (birefrinqent) waveplates. This is common practice in the visible, but in the infrared the very properties required to construct such a device are the properties the invention herein is intended to measure, and there is not an abundance of data available to readily design high performance devices of this kind.

Figure 4:
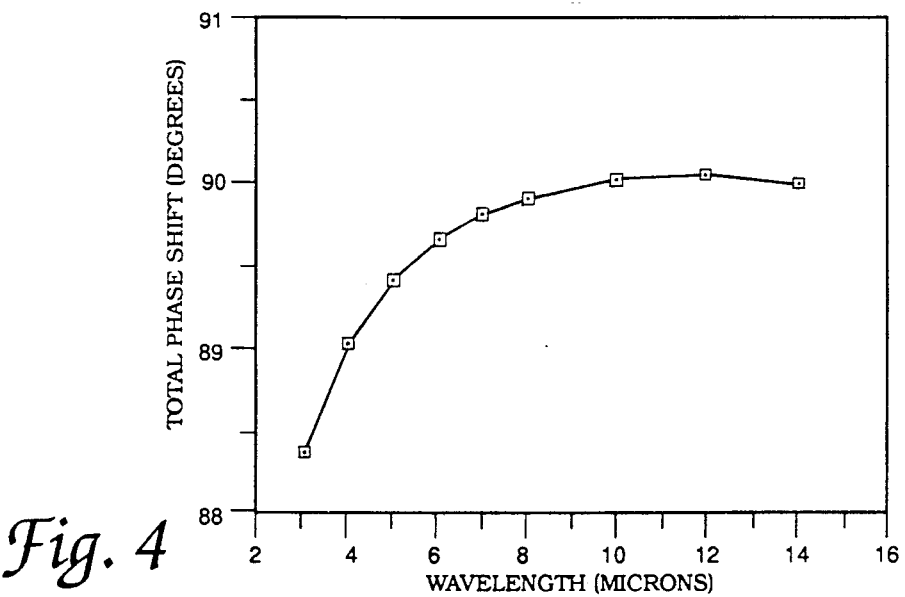
FIG. 4 is a graph of total phase shift versus wavelength for the FIG. 3 retarder.

The retarder described in the cross reference and depicted in FIG. 3 provides suitable achromatic infrared prism retarders 63,64 for use in system 10 of this invention. The retarder of the cross reference can produce a desired phase delay of one polarized light component with respect to the orthogonal component while maintaining colinear output and input beams i.e. without beam deviation. Each retarder 63,64 comprises two identical prisms 71,72 of zinc selenide, zinc sulfide, germanium, arsenic trisulfide glass, gallium arsenide or the like mounted in confronting relationship on a supporting reflective surface 73 of gold, silver. copper, lead, aluminum or the like. Each prism 71,72 is configured with a first optical surface 75 providing an entry window for light beam 15 disposed at a right angle (90°) to surface 76 resting on surface 73. Each prism 71,72 is further defined by optical surfaces 77,78, the angles between surfaces 75,77, between surfaces 77,78 and between surfaces 78,76 being defined according to the refractive index of material comprising prisms 71,72 to provide selected net phase shift, and the required phase retardance at the various prism/air interfaces. Region 79 defined between prisms 71,72 is open to ambient (air) bounded by surfaces 78 of prisms 71,72 and reflective surface 73. Using ZnSe prisms 71,72 having angles A,B of 64.77° with gold reflective surface 73 resulted in retardation very close to quarter wavelength in the 3–14 micron range as shown in the graph of total phase shift versus wavelength of FIG. 4. Although each retarder 63,64 may be undesirably long (about 3 inches depending on desired clear aperture) a nearly achromatic retarder with no beam deviation is provided.

Figure 5:
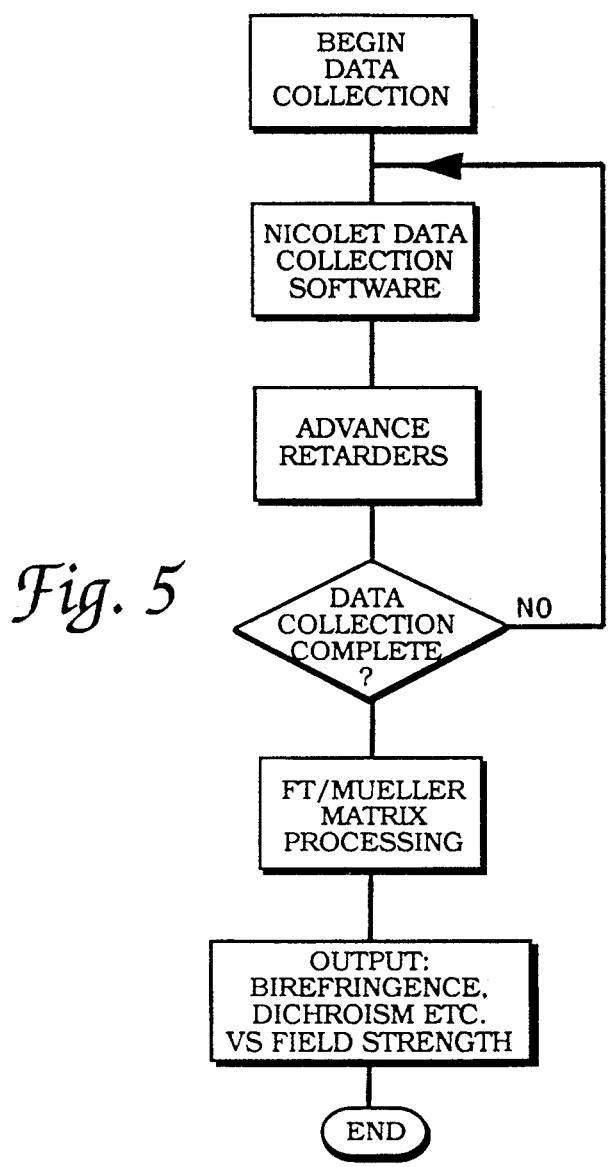
FIG. 5 is a block diagram illustrating the functions of representative computer software for collection and analysis of data for the FIG. 1 system.

Referring now to FIG. 5, shown therein is a block diagram of representative computer software useful for data collection and analysis in the operation of system 10. The current configuration of the Nicolet control computer program FTIR allows macro control of hardware and operation of data processing and collection routines. FORTRAN programs may be called from the macro as subroutines. Data files may also be managed from the macro, allowing the data to be stored on the Nicolet hard disk or transferred to another computer (e.g., a MicroVax) through the RS-232 port. The data collection software is maintained as a unit since, for a single retarder setting, system 10 operation will be substantially identical to that of the spectrometer.

In the operation of the software illustrated in FIG. 5, parameters and retarder settings are initialized and the first data set is taken as described in detail below. Retarders 63,64 are then rotated and another data set is taken, followed by further rotations until the required number of data sets is taken, the raw data being stored after each run. Data processing involves finding the Fourier transform and Mueller matrix defined hereinafter, resulting in birefringence or other information as output.

Two principal computational methods for treating polarization problems include the Jones calculus and the Mueller calculus. The Jones calculus is simpler and has the advantage of describing the absolute phase of the light, but will not readily treat problems involving depolarization and scattering of light while the Mueller calculus will. Mueller calculus is preferable for experimental work where scattering and depolarization should be routinely measured along with diattenuation and retardance. Jones calculus is preferable for analytical work particularly when depolarization is not being considered or is not part of the optical models.

In the Mueller calculus, the state of polarization of light is described by the Stokes four-element real vector, the four components of which describe the polarization ellipse of the light beam (three parameters) and degree of polarization of the light (one parameter). The Stokes vector describes the angular coherence of the electromagnetic wave, the amplitudes, phases and statistics of the transverse electromagnetic field components. The four Stokes vector components describe this angular coherence of a narrow spectral band light beam except for some higher order coherence properties of the light, polarizing elements are characterized by a 4×4 element real matrix. All elements of the Stokes vector and the Mueller matrix are real.

The invention measures the Mueller matrix of the sample $M_s(\lambda)$ as a function of wavelength. The polarizing elements in sample region 45 are two (approximately) quarter wave retarders $M_{R1}(\lambda,\theta_1)$ and $M_{R2}(\lambda,\theta_2)$ whose orientations $\theta_1$ and $\theta_2$ vary, and two linear polarizers $M_{P1}(\lambda)$ and $M_{P2}(\lambda)$ whose orientations remain fixed. The instrumental polarization effects of the Fourier transform spectrometer optics must be considered, including diattenuation and retardance due to mirror coatings and beamsplitter 29, if polarizers 60 and 61 are not ideal, i.e. if they transmit any light incident perpendicular to the transmission axis. Let $M_{I1}(\lambda)$ and $M_{I2}(\lambda)$ be the Mueller matrices for the optics before and after sample compartment 45a. The Mueller matrix equation which describes the optical system between source and detector is.

$$M_{sys}(\lambda,\theta_1,\theta_2) = M_{I2}(\lambda)M_{P2}(\lambda)M_{R2}(\lambda,\theta_2)M_s(\lambda)M_{R1}(\lambda,\theta_1)M_{P1}(\lambda)M_{I1}(\lambda)$$

The source has a spectral distribution and polarization state described by the wavelength dependent Stokes vector $S_{So}(\lambda)$, so the Stokes vector describing the light incident at the detector is $$S_D(\lambda,\theta_1,\theta_2) = M_{sys}(\lambda,\theta_1,\theta_2)S_{So}(\lambda)$$

The polarization spectra is acquired at a minimum of sixteen retarder orientations. From these polarization spectra, the Mueller matrix of the sample is determined. Various methods of obtaining the Mueller matrix from the sequences of measurements at various polarizer and retarder orientations may be used, such as that described by Azzam ("photopolarimetric measurement of the Mueller matrix by Fourier analysis of a single detected signal", Opt Lett 2.6 (1978)) or Hauge ("Mueller matrix ellipsometry with imperfect compensators", J Opt Soc Am 68,11 (1978)) where the retarders are both rotated simultaneously. The Mueller matrix elements are encoded on the different frequencies and phases of the modulated output intensity. This method allows for consistency checks to monitor polarimeter errors.

Retarders 63,64 are mounted in computer-controlled rotation stages so that the computer which controls the Fourier transform spectroscopy data collection and processing will make scans at one retarder setting, then automatically advance the retarders for the next set of scans, and so on. The result of this processing is the calculation of the Mueller matrix as a function of wavelength.

Figure 7:
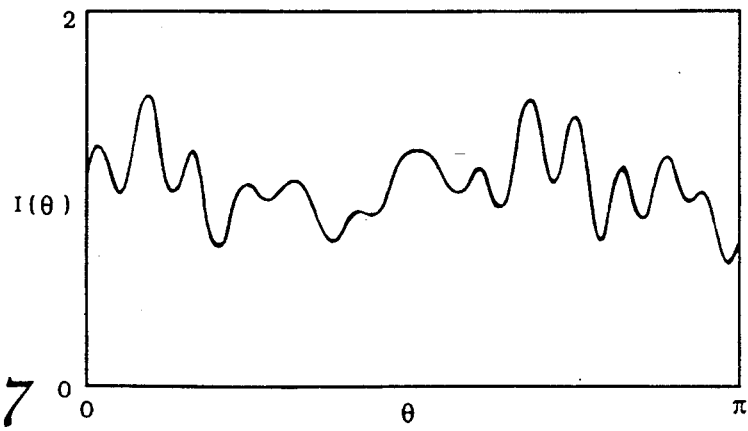
FIG. 7 is a graph of intensity versus angle for a simulated sample at a single wavelength.
Figure 6:
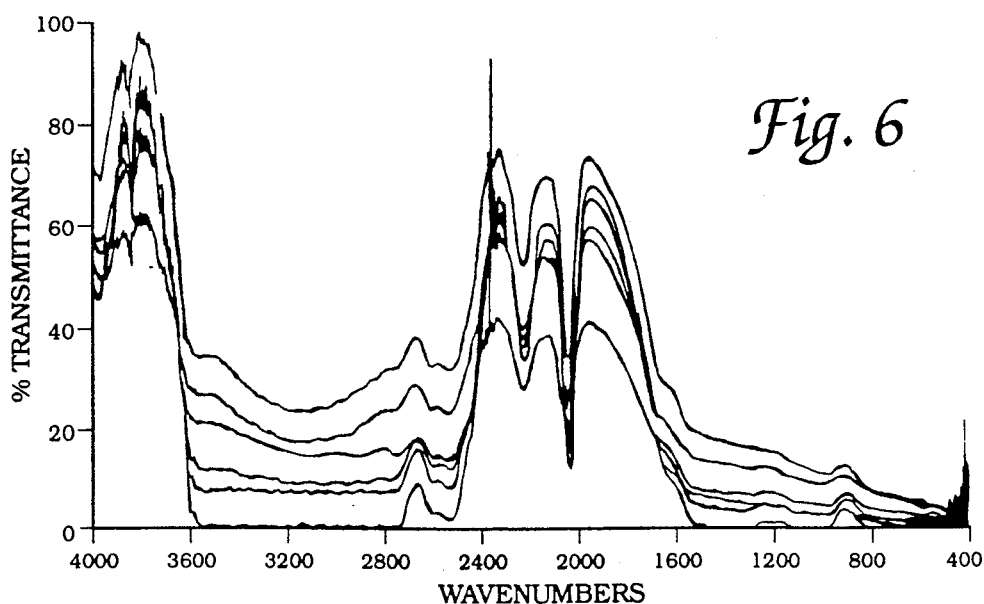
FIG. 6 shows graphs of per cent transmittance versus wave number at various retarder angles for a simulated sample.

FIG. 6 shows an example of the operation of the invention with simulated data. A set of spectra are acquired at various retarder settings. FIG. 7 shows a typical signal at one wavelength as retarders 63,64 are rotated by $5\theta$ and $\theta$. Mueller matrix elements are encoded on the intensity and phases of the frequency components of this graph. The data is reduced using the methods mentioned above assuming ideal polarization elements or more general algorithms to compensate for nonideal polarization behavior.

Calibration of system 10 is extremely important since orientational alignment errors of polarizing elements (polarizers) 60,61 can induce errors in the resultant measured Mueller matrices. Different combinations of alignment errors produce errors in different sets of Mueller matrix elements. Analytical expressions are derived for the Mueller matrix elements as a function of the alignment errors.

Figure 8:
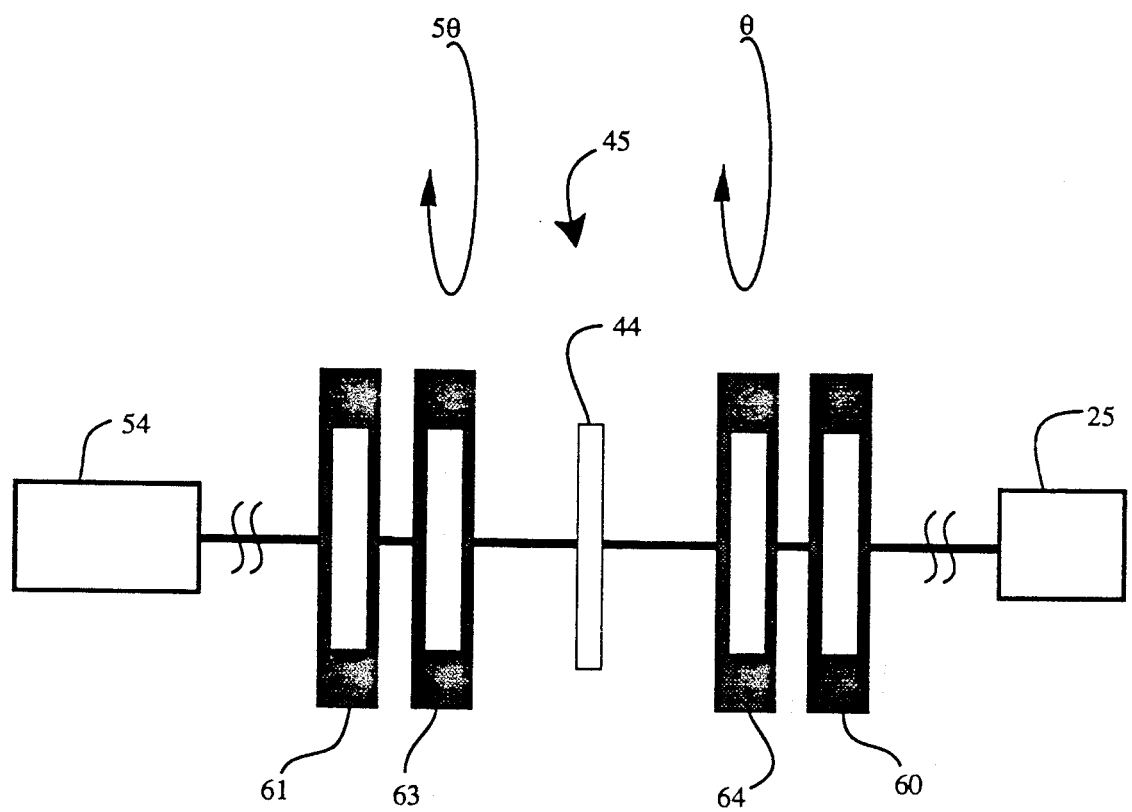
FIG. 8 is an illustration of the sample region of the system of FIG. 1 showing positioning and rotation of the retarders.

FIG. 8 shows sample region 45 of system 10 and positioning and rotation of polarizers 60,61. In the arrangement shown, retarders 63,64 are rotated harmonically and a periodic signal is generated. Experimentally, a set of intensity values is obtained at discrete intervals in angle. This signal can be expanded in a Fourier series. The rotation rates of the two retarders are related by a factor of five, i.e., $\theta_2 = 5\theta_1$, and the signal I is given by, $$I = a_0 + \sum_{n=1}^{12} (a_n \cos 2n\theta + b_n \sin 2n\theta)$$

where the Fourier coefficients $a_n$ and $b_n$ are functions of the Mueller matrix elements and $\theta$ is the rotation angle of retarder 64. A factor of two appears with the angle in the expansion because polarizers 60,61 repeat their behavior twice over one complete revolution. The equations for Fourier coefficients are inverted to give the Mueller matrix elements $m_{ij}$ presented below:

$$m_{11} = a_0 - a_2 + a_8 - a_{10} + a_{12}$$

$$m_{12} = 2a_2 - 2a_8 - 2a_{12}$$

$$m_{13} = 2b_2 + 2b_8 - 2b_{12}$$

$$m_{14} = b_1 - 2b_{11} = b_1 + 2b_9 = b_1 + b_9 - b_{11}$$

$$m_{21} = -2a_8 + 2a_{10} - 2a_{12}$$

$$m_{22} = 4a_8 + 4a_{12}$$

$$m_{23} = -4b_8 + 4b_{12}$$

$$m_{24} = -4b_9 = 4b_{11} = 2(-b_9 + b_{11})$$

$$m_{31} = -2b_8 + 2b_{10} - 2b_{12}$$

$$m_{32} = 4b_8 + 4b_{12}$$

$$m_{33} = 4a_8 - 4a_{12}$$

$$m_{34} = 4a_9 = -4a_{11} = 2(a_9 - a_{11})$$

$$m_{41} = 2b_3 - b_5 = -b_5 + 2b_7 = (b_3 - b_5 + b_7)$$

$$m_{42} = -4b_3 = -4b_7 = -2(b_3 + b_7)$$

$$m_{43} = -4a_3 = 4a_7 = 2(-a_3 + a_7)$$

$$m_{44} = -2a_4 = 2a_6 = (a_6 - a_4)$$

For calibration and data acquisition purposes, expressions given below for the Fourier coefficients a and b with errors with matrix elements of the identity matrix inserted for the Mueller matrix elements are used, given experimentally measured coefficients with no sample present, to calculate values for the errors in element orientations and retardances. In routine use of the invention, systematic errors arising from imperfections are compensated using inversions of the expressions below for a and b with experimentally determined error values to obtain the sample Mueller matrix elements as functions of measured Fourier coefficients.

Consider the errors associated with measurements taken using the invention for sample region 45 including polarizers 60,61. In this analysis it is assumed that no angular errors are associated with stages which rotate retarders 63,64 and that only relative orientations of polarizers 60,61 and retarders 63,64 are relevant to the analysis, and effects of retardation associated with polarizers 60,61 and polarization associated with retarders 63,64 are not considered. All angles are measured relative to first polarizer 60. Remaining elements 61,63,64 may have errors associated with an initial azimuthal alignment relative to polarizer 60, and retarders 63,64 different retardances different from quarter-wave.

The Mueller matrix for the system including polarizers 60,61, retarders 63,64 and sample 44 can be expressed as, $$L_2 R_2(\theta) M R_1(\theta) L_1$$

where $L_1, L_2$ characterize linear polarizers 60,61, $R_1, R_2$ characterize linear retarders 63,64 and M characterizes sample 44. Substitution is then made of Mueller matrices for linear retarders with some retardation and a fast axis at angles for $R_1$ and $R_2$, a linear polarizer at an angle for $P_2$, a linear horizontal polarizer for $P_1$ and a sample for M. The Mueller matrices as functions of retardation and orientation angles for an ideal linear polarizer at angle $\theta$ may be expressed as, $$\frac{1}{2}\begin{bmatrix} 1 & \cos 2\theta & \sin 2\theta & 0 \\ \cos 2\theta & \cos^2 2\theta & \cos 2\theta \sin 2\theta & 0 \\ \sin 2\theta & \cos 2\theta \sin 2\theta & \sin^2 2\theta & 0 \\ 0 & 0 & 0 & 0 \end{bmatrix}$$

and for a linear retarder with retardation $\delta$ and fast axis at angle $\theta$ as, $$\begin{bmatrix} 1 & 0 & 0 & 0 \\ 0 & \cos^2 2\theta + \sin^2 2\theta \cos\delta & \cos 2\theta \sin 2\theta (1 - \cos\delta) & -\sin 2\theta \sin\delta \\ 0 & \cos 2\theta \sin 2\theta (1 - \cos\delta) & \sin^2 2\theta + \cos^2 2\theta \cos\delta & \cos 2\theta \sin\delta \\ 0 & \sin 2\theta \sin\delta & -\cos 2\theta \sin\delta & \cos\delta \end{bmatrix}$$

(see e.g., Azzam, supra). The detected intensity through sample region 45 is given by, $$I = c \, A \, M \, P$$

where $P = R_1 L_1 S$ is the Stokes vector of light leaving the polarizing optics with S being the Stokes vector of light from the source, $A = L_2 R_2$ is the first row of the Mueller matrix of the analyzing optics, M is the Mueller matrix of the sample, and c is a proportionality constant obtained from the absolute intensity, $$I = c \sum_{i,j=1}^{4} a_i p_j m_{ij}$$

or, $$I = c \sum_{i,j=1}^{4} \mu_{ij} m_{ij}$$

where, $\mu_{ij} = a_i p_j$, and $m_{ij}$ are elements of M. For a spectropolarimeter where the last three elements have azimuthal alignment errors, elements $\mu_{ij}$ are as follows, where $\delta_1$ and $\delta_2$ are respective retardations of the first and second waveplates, $\epsilon_3$ and $\epsilon_4$ are respective azimuthal errors of the first and second waveplates and $\epsilon_5$ is the azimuthal error of the second polarizer:

$$\mu_{11} = \frac{1}{2}$$

$$\mu_{12} = \frac{1}{2}(\cos^2 2(\theta + \epsilon_3) + \sin^2 2(\theta + \epsilon_3)\cos\delta_1)$$

$$\mu_{13} = \frac{1}{2}\cos 2(\theta + \epsilon_3)\sin 2(\theta + \epsilon_3)(1 - \cos\delta_1)$$

Figure 9:
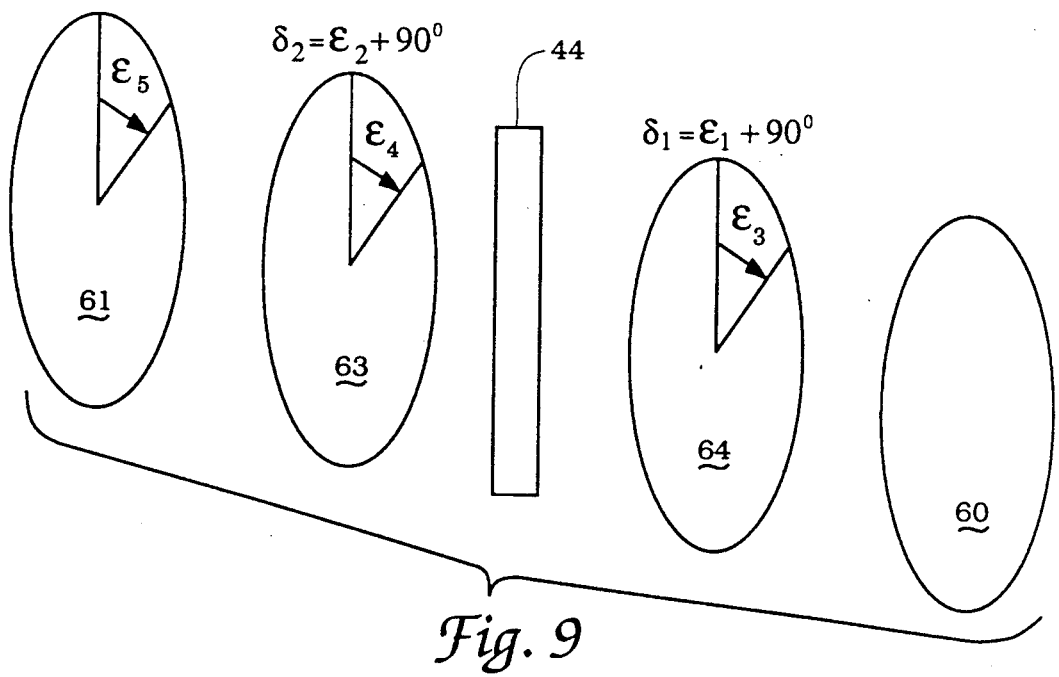
FIG. 9 illustrates the polarization elements of the system of FIG. 1 together with their associated errors.

-continued $\mu_{14} = \frac{1}{2}\sin\delta_1\sin 2(\theta + \epsilon_3)$ $\mu_{21} = \frac{1}{2}(\cos 2\epsilon_5(\cos^2 10(\theta + \epsilon_4) + \sin^2 10(\theta + \epsilon_4)\cos\delta_2) +$
$\qquad \sin 2\epsilon_5 \cos 10(\theta + \epsilon_4)\sin 10(\theta + \epsilon_4)(1 - \cos\delta_2))$ $\mu_{22} = \frac{1}{2}[\cos 2\epsilon_5(\cos^2 10(\theta + \epsilon_4) + \sin^2 10(\theta + \epsilon_4)\cos\delta_2) +$
$\qquad \sin 2\epsilon_5 \cos 10(\theta + \epsilon_4)\sin 10(\theta + \epsilon_4)(1 - \cos\delta_2)] \times$
$\qquad\qquad (\cos^2 2(\theta + \epsilon_3) + \sin^2 2(\theta + \epsilon_3)\cos\delta_1)$ $\mu_{23} = \frac{1}{2}[\cos 2\epsilon_5(\cos^2 10(\theta + \epsilon_4) + \sin^2 10(\theta + \epsilon_4)\cos\delta_2) +$
$\qquad \sin 2\epsilon_5 \cos 10(\theta + \epsilon_4)\sin 10(\theta + \epsilon_4)(1 - \cos\delta_2)] \times$
$\qquad\qquad \cos 2(\theta + \epsilon_3)\sin 2(\theta + \epsilon_3)(1 - \cos\delta_1)$ $\mu_{24} = \frac{1}{2}[\cos 2\epsilon_5(\cos^2 10(\theta + \epsilon_4) + \sin^2 10(\theta + \epsilon_4)\cos\delta_2) +$
$\qquad \sin 2\epsilon_5 \cos 10(\theta + \epsilon_4)\sin 10(\theta + \epsilon_4)(1 - \cos\delta_2)] \times \sin 2(\theta + \epsilon_3)\sin\delta_1$ $\mu_{31} = \frac{1}{2}[\cos 2\epsilon_5\cos 10(\theta + \epsilon_4) + \sin 10(\theta + \epsilon_4)(1 - \cos\delta_2) +$
$\qquad \sin 2\epsilon_5(\sin^2 10(\theta + \epsilon_4) + \cos^2 10(\theta + \epsilon_4)\cos\delta_2))$ $\mu_{32} = \frac{1}{2}[\cos 2\epsilon_5\cos 10(\theta + \epsilon_4)\sin 10(\theta + \epsilon_4)(1 - \cos\delta_2) +$
$\qquad \sin 2\epsilon_5(\sin^2 10(\theta + \epsilon_4) + \cos^2 10(\theta + \epsilon_4)\cos\delta_2)] \times$
$\qquad\qquad (\cos^2 2(\theta + \epsilon_3) + \sin^2 2(\theta + \epsilon_3)\cos\delta_1)$ $\mu_{33} = \frac{1}{2}[\cos 2\epsilon_5\cos 10(\theta + \epsilon_4)\sin 10(\theta + \epsilon_4)(1 - \cos\delta_2) +$
$\qquad \sin 2\epsilon_5(\sin^2 10(\theta + \epsilon_4) + \cos^2 10(\theta + \epsilon_4)\cos\delta_2)] \times$
$\qquad\qquad \cos 2(\theta + \epsilon_3)\sin 2(\theta + \epsilon_3)(1 - \cos\delta_1)$ $\mu_{34} = \frac{1}{2}[\cos 2\epsilon_5\cos 10(\theta + \epsilon_4)\sin 10(\theta + \epsilon_4)(1 - \cos\delta_2) +$
$\qquad \sin 2\epsilon_5(\sin^2 10(\theta + \epsilon_4) + \cos^2 10(\theta + \epsilon_4)\cos\delta_2)] \times$
$\qquad\qquad \sin 2(\theta + \epsilon_3)\sin\delta_1$ $\mu_{41} = \frac{1}{2}(-\cos 2\epsilon_5 \sin 10(\theta + \epsilon_4)\sin\delta_2 + \sin 2\epsilon_5\cos 10(\theta + \epsilon_4)\sin\delta_2)$ $\mu_{42} = \frac{1}{2}((-\cos 2\epsilon_5)\sin 10(\theta + \epsilon_4)\sin\delta_2 +$
$\qquad \sin 2\epsilon_5\cos 10(\theta + \epsilon_4)\sin\delta_2) \times (\cos^2 2(\theta + \epsilon_3) + \sin^2 2(\theta + \epsilon_3)\cos\delta_1)$ $\mu_{43} = \frac{1}{2}((-\cos 2\epsilon_5)\sin 10(\theta + \epsilon_4)\sin\delta_2 +$
$\qquad \sin 2\epsilon_5\cos 10(\theta + \epsilon_4)\sin\delta_2) \times \cos 2(\theta + \epsilon_3)\sin 2(\theta + \epsilon_3)(1 - \cos\delta_1)$ $\mu_{44} = \frac{1}{2}((-\cos 2\epsilon_5)\sin 10(\theta + \epsilon_4)\sin\delta_2 +$
$\qquad \sin 2\epsilon_5\cos 10(\theta + \epsilon_4)\sin\delta_2) \times \sin 2(\theta + \epsilon_3)\sin\delta_1$ Since a system operated in demonstration of the invention includes quarter-wave retarders, $\delta_1 = 90° + \epsilon_1$ and $\delta_2 = 90° + \epsilon_2$ where $\epsilon_1$ and $\epsilon_2$ are the retardation errors of retarders 63, 64, respectively. FIG. 9 illustrates the polarization elements of the system of FIG. 1 together with associated errors.

Having obtained $\mu_{ij}$ as set forth above, another Fourier expansion is made and a new set of coefficients obtained as functions of the error angles. New total coefficients for each harmonic are obtained from a sum of coefficients of common harmonics over all $\mu_{ij}$, namely, $a_0 = \frac{1}{2}m_{11} + \left[\frac{\cos\delta_1 + 1}{4}\right]m_{12} +$ $\qquad \left[\frac{(\cos\delta_2 + 1)\cos 2\epsilon_5}{4}\right]m_{21} +$ $\qquad \left[\frac{(\cos\delta_1 + 1)(\cos\delta_2 + 1)\cos 2\epsilon_5}{8}\right]m_{22} +$ $\qquad \left[\frac{(\cos\delta_2 + 1)\sin 2\epsilon_5}{4}\right]m_{31} +$ $\qquad \left[\frac{(\cos\delta_1 + 1)(\cos\delta_2 + 1)\sin 2\epsilon_5}{8}\right]m_{32}$ $a_1 = \left[\frac{\sin\delta_1\sin 2\epsilon_3}{4}\right]m_{14} +$ $\qquad \left[\frac{\sin\delta_1(\cos\delta_2 + 1)\sin 2\epsilon_3\cos 2\epsilon_5}{4}\right]m_{24} +$ $\qquad \left[\frac{\sin\delta_1(\cos\delta_2 + 1)\sin 2\epsilon_3\sin 2\epsilon_5}{4}\right]m_{34}$ $a_2 = \left[\frac{(1 - \cos\delta_1)\cos 4\epsilon_3}{4}\right]m_{12} +$ $\qquad \left[\frac{(1 - \cos\delta_1)\sin 4\epsilon_3}{4}\right]m_{13} +$ $\qquad \left[\frac{(1 - \cos\delta_1)(1 - \cos\delta_2)\cos 4\epsilon_3\cos 2\epsilon_5}{8}\right]m_{22} -$ $\qquad \left[\frac{(1 - \cos\delta_1)(\cos\delta_2 - 1)\sin 4\epsilon_3\cos 2\epsilon_5}{8}\right]m_{23} -$ $\qquad \left[\frac{(1 - \cos\delta_1)(1 + \cos\delta_2)\cos 4\epsilon_3\sin 2\epsilon_5}{8}\right]m_{32} +$ $\qquad \left[\frac{(1 - \cos\delta_1)(\cos\delta_2 + 1)\sin 4\epsilon_3\sin 2\epsilon_5}{8}\right]m_{33}$ $a_3 = \left[\frac{(\cos\delta_1 - 1)\sin\delta_2\sin(10\epsilon_4 - 4\epsilon_3 - 2\epsilon_5)}{8}\right]m_{42} -$ $\qquad \left[\frac{(\cos\delta_1 - 1)\sin\delta_2\cos(2\epsilon_4 - 10\epsilon_3 + 4\epsilon_5)}{8}\right]m_{43}$ $a_4 = \left[\frac{-\sin\delta_1\sin\delta_2\cos(10\epsilon_4 - 2\epsilon_3 - 2\epsilon_5)}{4}\right]m_{44}$ $a_5 = \left[\frac{(\sin\delta_2\sin(2\epsilon_5 - 10\epsilon_4)}{2}\right]m_{41} +$ $\qquad \left[\frac{(\cos\delta_1 + 1)\sin\delta_2\sin(2\epsilon_5 - 10\epsilon_4)}{4}\right]m_{42}$ $a_6 = \left[\frac{\sin\delta_1\sin\delta_2\cos(10\epsilon_4 + 2\epsilon_3 - 2\epsilon_5)}{4}\right]m_{44}$ $a_7 = \left[\frac{(\cos\delta_1 - 1)\sin\delta_2\sin(10\epsilon_4 + 4\epsilon_3 - 2\epsilon_5)}{8}\right]m_{42} +$ $$\left[\frac{-(\cos\delta_1 - 1)\sin\delta_2\cos(10\epsilon_4 + 4\epsilon_3 - 2\epsilon_5)}{8}\right]m_{43}$$

$$a_8 = \left[\frac{(1 - \cos\delta_1)(1 - \cos\delta_2)\cos(20\epsilon_4 - 4\epsilon_3 - 2\epsilon_5)}{16}\right](m_{22} + m_{33}) +$$

$$\left[\frac{(1 - \cos\delta_1)(1 - \cos\delta_2)\sin(20\epsilon_4 - 4\epsilon_3 - 2\epsilon_5)}{16}\right](m_{32} - m_{23})$$

$$a_9 = \left[\frac{\sin\delta_1(1 - \cos\delta_2)\sin(2\epsilon_5 - 20\epsilon_4 + 2\epsilon_3)}{8}\right]m_{24} +$$

$$\left[\frac{\sin\delta_1(1 - \cos\delta_2)\cos(2\epsilon_5 - 20\epsilon_4 + 2\epsilon_3)}{8}\right]m_{34}$$

$$a_{10} = \left[\frac{(1 - \cos\delta_2)\cos(20\epsilon_4 - 2\epsilon_5)}{4}\right]m_{21} +$$

$$\left[\frac{(\cos\delta_1 + 1)(1 - \cos\delta_2)\cos(20\epsilon_4 - 2\epsilon_5)}{8}\right]m_{22} +$$

$$\left[\frac{(1 - \cos\delta_2)\sin(20\epsilon_4 - 2\epsilon_5)}{4}\right]m_{31} +$$

$$\left[\frac{(\cos\delta_1 + 1)(1 - \cos\delta_2)\sin(20\epsilon_4 - 2\epsilon_5)}{8}\right]m_{32}$$

$$a_{11} = \left[\frac{\sin\delta_1(\cos\delta_2 - 1)\sin(20\epsilon_5 - 20\epsilon_4 - 2\epsilon_3)}{8}\right]m_{24} +$$

$$\left[\frac{\sin\delta_1(\cos\delta_2 - 1)\cos(2\epsilon_5 - 20\epsilon_4 - 2\epsilon_3)}{8}\right]m_{34}$$

$$a_{12} =$$

$$\left[\frac{(1 - \cos\delta_1)(1 - \cos\delta_2)\cos(4\epsilon_3 + 20\epsilon_4 - 2\epsilon_5)}{16}\right](m_{22} - m_{33}) +$$

$$\left[\frac{(1 - \cos\delta_1)(1 - \cos\delta_2)\sin(4\epsilon_3 + 20\epsilon_4 - 2\epsilon_5)}{16}\right](m_{23} + m_{32})$$

$$b_1 = \left[\frac{\sin\delta_1\cos 2\epsilon_3}{2}\right]m_{14} +$$

$$\left[\frac{\sin\delta_1(\cos\delta_2 + 1)\cos 2\epsilon_3\cos 2\epsilon_5}{4}\right]m_{24} +$$

$$\left[\frac{\sin\delta_1(\cos\delta_2 + 1)\cos 2\epsilon_3\sin 2\epsilon_5}{4}\right]m_{34}$$

$$b_2 = \left[\frac{(\cos\delta_1 - 1)\sin 4\epsilon_3}{4}\right]m_{12} +$$

$$\left[\frac{(1 - \cos\delta_1)\cos 4\epsilon_3}{4}\right]m_{13} +$$

$$\left[\frac{(1 - \cos\delta_1)(1 + \cos\delta_2)\cos 4\epsilon_3\cos 2\epsilon_5}{8}\right]m_{23} +$$

$$\left[\frac{-(1 - \cos\delta_1)(\cos\delta_2 + 1)\sin 4\epsilon_3\cos 2\epsilon_5}{8}\right]m_{22} +$$

$$\left[\frac{(1 - \cos\delta_1)(1 + \cos\delta_2)\cos 4\epsilon_3\sin 2\epsilon_5}{8}\right]m_{33} +$$

$$\left[\frac{-(1 - \cos\delta_1)(\cos\delta_2 + 1)\sin 4\epsilon_3\sin 2\epsilon_5}{8}\right]m_{32}$$

$$b_3 = \left[\frac{(\cos\delta_1 - 1)\sin\delta_2\cos(2\epsilon_5 - 10\epsilon_4 + 4\epsilon_3)}{8}\right]m_{42} -$$

$$\left[\frac{(\cos\delta_1 - 1)\sin\delta_2\sin(10\epsilon_4 - 4\epsilon_3 - 2\epsilon_5)}{8}\right]m_{43}$$

$$b_4 = \left[\frac{\sin\delta_1\sin\delta_2\sin(10\epsilon_4 - 2\epsilon_3 - 2\epsilon_5)}{4}\right]m_{44}$$

$$b_5 = \left[\frac{-\sin\delta_2\cos(10\epsilon_4 - 2\epsilon_5)}{2}\right]m_{41} +$$

$$\left[\frac{-(\cos\delta_1 + 1)\sin\delta_2\cos(2\epsilon_5 - 10\epsilon_4)}{4}\right]m_{42}$$

$$b_6 = \left[\frac{\sin\delta_1\sin\delta_2\sin(2\epsilon_5 - 2\epsilon_3 - 10\epsilon_4)}{4}\right]m_{44}$$

$$b_7 = \left[\frac{(\cos\delta_1 - 1)\sin\delta_2\cos(10\epsilon_4 + 4\epsilon_3 - 2\epsilon_5)}{8}\right]m_{42} +$$

$$\left[\frac{(\cos\delta_1 - 1)\sin\delta_2\sin(10\epsilon_4 + 4\epsilon_3 - 2\epsilon_5)}{8}\right]m_{43}$$

$$b_8 =$$

$$\left[\frac{-(1 - \cos\delta_1)(1 - \cos\delta_2)\sin(20\epsilon_4 - 4\epsilon_3 - 2\epsilon_5)}{16}\right](m_{22} + m_{33}) +$$

$$\left[\frac{(1 - \cos\delta_1)(1 - \cos\delta_2)\cos(20\epsilon_4 - 4\epsilon_3 - 2\epsilon_5)}{16}\right](m_{23} - m_{32})$$

$$b_9 = \left[\frac{\sin\delta_1(\cos\delta_2 - 1)\cos(20\epsilon_4 - 2\epsilon_3 - 2\epsilon_5)}{8}\right]m_{24} +$$

$$\left[\frac{\sin\delta_1(\cos\delta_2 - 1)\sin(20\epsilon_4 - 2\epsilon_3 - 2\epsilon_5)}{8}\right]m_{34}$$

$$b_{10} = \left[\frac{(\cos\delta_2 - 1)\sin(20\epsilon_4 - 2\epsilon_5)}{4}\right]m_{21} +$$

$$\left[\frac{(\cos\delta_1 + 1)(\cos\delta_2 - 1)\sin(20\epsilon_4 - 2\epsilon_5)}{8}\right]m_{22} +$$

$$b_{11} = \left[\frac{(1-\cos\delta_2)\cos(20\epsilon_4-2\epsilon_5)}{4}\right]m_{31} +$$

$$\left[\frac{(\cos\delta_1+1)(1-\cos\delta_2)\cos(20\epsilon_4-2\epsilon_5)}{8}\right]m_{32}$$

$$\left[\frac{\sin\delta_1(1-\cos\delta_2)\cos(20\epsilon_4+2\epsilon_3-2\epsilon_5)}{8}\right]m_{24} +$$

$$\left[\frac{\sin\delta_1(1-\cos\delta_2)\sin(20\epsilon_4+2\epsilon_3-2\epsilon_5)}{9}\right]m_{34}$$

$$b_{12} =$$

$$\left[\frac{(1-\cos\delta_1)(1-\cos\delta_2)\sin(20\epsilon_4+4\epsilon_3-2\epsilon_5)}{16}\right](m_{22}-m_{33}) +$$

$$\left[\frac{(1-\cos\delta_1)(1-\cos\delta_2)\cos(20\epsilon_4+4\epsilon_3-2\epsilon_5)}{16}\right](m_{32}+m_{23})$$

The new Mueller matrix elements are then found from inversions of the expressions for a and b just presented using the measured coefficients. It is noted that the calibration procedure for the invention may be used to detect alignment errors, and these errors can then be determined using a least squares procedure. Angular alignments can be corrected and retardance errors compensated for. In this way, highly accurate values of the Mueller matrix elements are obtainable.

The invention therefore provides an infrared spectropolarimeter system for making spectroscopic measurements of electro-optical properties of material samples over an extended continuous infrared spectral range as a function of applied electromagnetic field, and which allows rapid acquisition of accurate data not heretofore obtainable. It is understood that modifications to the invention may be made as might occur to one skilled in the field of the invention within the scope of the appended claims. All embodiments contemplated hereunder which achieve the objects of the invention have therefore not been shown in complete detail. Other embodiments may be developed without departing from the spirit of the invention or from the scope of the appended claims.

We claim:

1. An infrared spectropolarimeter system for making spectroscopic measurements of electro-optic properties of materials over a large wavelength range in the infrared, comprising:
   (a) a Fourier transform infrared spectrometer having a sample region for receiving a sample for making spectroscopic measurement thereon and a source of light for providing a sample beam of selected wavelength range in the infrared for projection through said sample region, said sample region defined between first and second focusing elements, said first focusing element disposed for selectively focusing said sample beam within said sample region, said second focusing element disposed for collimating said sample beam and providing an output beam for analysis;
   (b) first and second polarizers disposed between said first and second focusing elements with said sample region therebetween, for selectively polarizing said sample beam;
   (c) first and second rotatable optical retarders disposed between said first and second polarizers with said sample region therebetween, for selectively retarding one linear polarization component of said sample beam with respect to the orthogonal component of said sample beam;
   (d) means for controllably rotating said first and second optical retarders; and
   (e) detection means for analyzing said output beam.

2. The system of claim 1 wherein said first and second polarizers are wire grid polarizers.

3. The system of claim 1 further comprising means for imposing an electric field of preselected field strength on said sample region for determining spectroscopic electrooptic properties of a sample as functions of electric field strength.

4. The system of claim 1 further comprising means for imposing a magnetic field of preselected field strength on said sample region for determining spectroscopic electrooptic properties of a sample as functions of magnetic field strength.

* * * * *